United States Patent
Reid et al.

(10) Patent No.: US 6,372,124 B2
(45) Date of Patent: Apr. 16, 2002

(54) REMOVAL OF IMPURITIES FROM HYDROCARBON STREAMS

(75) Inventors: John S. Reid, Wooster; Thomas Szymanski, Hudson, both of OH (US); Shaun A. Mesher, Calgary (CA)

(73) Assignee: Saint-Gobain Norpro Corporation, Stow, OH (US)

( * ) Notice: Subject to any disclaimer, the term of this patent is extended or adjusted under 35 U.S.C. 154(b) by 0 days.

(21) Appl. No.: 09/782,776

(22) Filed: Feb. 13, 2001

Related U.S. Application Data

(63) Continuation-in-part of application No. 09/476,898, filed on Jan. 3, 2000, now Pat. No. 6,207,612.

(51) Int. Cl.⁷ ........................ C10G 19/00; C10G 29/04; C10G 17/00

(52) U.S. Cl. ................... 208/203; 208/251 R; 208/253; 208/283; 208/284; 208/288; 208/289

(58) Field of Search ............................. 208/251 R, 253, 208/283, 299, 203, 284, 288

(56) References Cited

U.S. PATENT DOCUMENTS 4,147,665 A * 4/1979 Ikari et al. .................. 502/415
5,268,091 A * 12/1993 Boitiaux et al. ........ 208/251 R

* cited by examiner

*Primary Examiner*—Mark L. Bell
*Assistant Examiner*—Patricia L. Hailey
(74) *Attorney, Agent, or Firm*—David Bennett

(57) ABSTRACT

The invention provides a method of purifying hydrocarbon streams from metallic impurities which comprises passing the stream through media comprising alumina with relatively minor amounts of calcia and magnesia.

5 Claims, No Drawings

REMOVAL OF IMPURITIES FROM HYDROCARBON STREAMS

This Application is a continuation-in-part of application Ser. No. 09/476,898 filed Jan. 3, 2000, now U.S. Pat. No. 6,207,612, which describes the discovery of certain media useful in the separation of certain acidic impurities from crude hydrocarbon flows. This Application arises from the discovery of another important application for such media in the removal of metallic impurities from hydrocarbon streams.

BACKGROUND OF THE INVENTION

The present invention relates to the treatment of hydrocarbon streams using adsorbent material that is effective to remove troublesome metallic components often present in such streams.

Hydrocarbon streams generated within a refinery often contain metallic impurities in the form of organic or inorganic compounds of the metal or in the form of the metal itself. These metallic impurities can cause significant problems such as catalyst deactivation, degradation of properties of metals used in the processing equipment, environmental pollution and toxic contamination. It is therefore highly desirable to remove these materials form the streams to avoid or mitigate such effects.

SUMMARY OF THE INVENTION

The invention provides a method of removing metallic impurities from a hydrocarbon stream which comprises contacting the stream with media which comprise from 50 to 96% by weight of alumina and from 50 to 4% by weight of alkaline earth metal oxides selected from calcia and magnesia in CaO:MgO proportions by weight of from 90:10 to 50:50, and have a BET surface area of at least 100 m²/gm. The hydrocarbon stream is preferably contacted with the media at a temperature between 20° C. and 450° C. and preferably between 250° C. and 350° C.

The metals removed from petroleum streams using the media according to the invention include lead, copper, aluminum, silicon, iron, chromium, zinc, magnesium, nickel, sodium, calcium, vanadium, mercury phosphorus and manganese. As a general rule the hydrocarbon stream contains hydrocarbons with five or more carbon atoms.

The term "media" as used herein is intended to ceramic materials having the above composition in the shape of pellets, balls, rods or other shapes having sufficient porosity, (as reflected in the surface area), to cause the metallic impurities to be physically trapped within the pores of the medium, adsorbed on to the surface of the pores of the medium, or, more usually to react chemically with the material of the medium to produce components that are not further transported by the flow of which the impurity was a component.

The proportions of the components are calculated of the basis of the weights of components added initially stoichiometrically adjusted to the oxides that remain after firing to produce the media of the invention. In general terms this gives a reasonably accurate translation as can be seen from the following chart.

| Boehmite | CaCO$_3$ | MgCO$_3$ | → | Al$_2$O$_3$ | CaO | MgO |
|---|---|---|---|---|---|---|
| 90 | 8.2 | 1.8 | | 92.2 | 6.6 | 1.2 |
| 60 | 36 | 4 | | 65.9 | 31.1 | 3.0 |
| 96 | 3.6 | 0.4 | | 97.1 | 2.6 | 0.3 |
| 96 | 2.0 | 2.0 | | 97 | 1.6 | 1.4 |

The first three formulations were made using dolomitic limestone and the fourth used plain dolomite. As can be seen the relative proportions do not change very significantly when going from the precursor materials to the final fired product.

The media can have any desired shape depending on the application. They can for example be in the form of short rods or pellets, hollow cylinders, rings, saddles and the like. A particularly useful shape is described in U.S. Pat. No. 5,304,423. Alternatively they can have the form of monoliths with multiple through passages that can be assembled into beds. Such monolith media are however often less preferred for applications such as those primarily intended for the media of the present invention.

It is believed that a major component mechanism for the removal of the metal from the hydrocarbon stream is based on the reaction of the metal with the media. When both the metal and the media are both polar in a non-polar liquid, (the hydrocarbon stream), the adsorption of the metal on the media surface is accelerated. Heat has been shown to accelerate this process. The activity of the media can be regenerated through removal of chemically retained impurities. This can be done by back-flushing a bed comprising media whose activity has declined with hot, (about 150° C. for example), steam. Removal that is essentially complete by continuing the steam treatment fo about eight hours. Prior to reactivation as outlined above it is desirable to remove heavy hydrocarbon residues trapped within the pores of the media using a hydrocarbon solvent such as toluene or an aromatic-rich solvent such a XYSOL™ (available from Trysol Canada Ltd. Of Calgary, Canada), preferably heated to a temperature of about 300° C.

It has been found that the use of a hot methanol wash, (at about 150° C. for example), between the solvent wash and the steam treatment helped clear out any residual oil and helps the steam penetrate the pores. The same effect can be achieved by the incorporation of a proportion of methanol in the steam. While methanol is particular effective, it is believed that any low molecular weight alcohol, such as ethanol or (n- or iso-) propanol could be substituted.

The media can be made by a method which comprises a) forming an aqueous slurry mixture of from 50–97% by weight of a hydrated alumina component, such as for example a boehmite, with from 50 to 3% by weight of a mixture of calcium carbonate and magnesium carbonate wherein the relative weight proportions of the calcium and magnesium carbonates are from 10:1 to 50:50, the weights of the boehmite and carbonate mixture being based on the solids weight in the slurry;

b) peptizing the slurry by addition of an acid;

c) extruding the peptized slurry to form the desired media shapes; and d) drying to remove water and then firing the shapes at a temperature of 650 to 850° C.

The hydrated alumina component can be selected, for example, from any of the commercial boehmite products which are commonly assigned the formula AlOOH or more accurately Al$_2$O$_3$.H$_2$O.

The mixture of calcium and magnesium carbonates is conveniently supplied by a powdered form of dolomite or preferably dolomitic limestone, which is a mixture of dolomite, (in which the calcium and magnesium metal atoms are present in nominally equal numbers) and calcite, with the calcite predominating and a few percentage points of impurities such a s silica and iron. When calcined during the firing stage this mixture decomposes to the respective oxides. The products of the invention could therefore, in theory, be made by incorporating the oxides or hydroxides into the boehmite slurry. This would however require more acid to peptize the slurry and thus is a less preferred option.

To aid dispersion of the carbonates in the boehmite sol, it is preferred that they be supplied in the form of a powder of about 50 microns average particle size or finer. A commercial dolomitic limestone that is commercially available from National Lime and Stone Company under the trade name Bucyrus Microfine, (99% passing through 325 mesh screen), is particularly suitable. This material contains the calcium and magnesium carbonates in a roughly 6:1 weight ratio The acid added to cause peptization of the slurry, which is essentially a dispersion of the calcium/magnesium-containing component in a boehmite sol, can be any of those generally know to peptize such sols. Because the firing would lead to decomposition of the acid, it is preferred that mineral acids such as nitric, hydrochloric or sulfuric acids be avoided and a strong organic acid such as acetic or, better, formic acid is used to cause peptization. The peptized sol in effect becomes a stable gel which can be formed, for example by extrusion, to produce shapes that will retain their shape during drying and firing. Enough is preferably added to reduce the pH to 5 or lower.

The drying of the shapes is preferably carried out under conditions that will allow the water to be removed without disruption of the shape. This implies drying at a fairly low temperature of about 100° C. (though up to 50° C. higher can be used in most circumstances) for prolonged periods of up to two days though usually a drying period of 10–24 hours is adequate.

Firing of the dried shapes should be long enough to form calcium and magnesium oxides from their respective carbonates and to drive off any bound water and convert the boehmite to the gamma alumina form of some other intermediate allomorph or amorphous form. It is however preferred that the firing should not be under conditions that would lead to the formation of the alpha form or sintering since this leads to a loss of porosity and leaves the alumina in a less active form. The firing temperature therefore is preferably at a maximum temperature of from 500 to 800° C. and for a period until no further loss of weight occurs. Generally heating at the firing temperature for 30 minutes to 5 hours is enough to decompose essentially all the carbonate and drive off all the bound water.

The surface area of the fired product is at least 100 $m^2$/gm such as above about 200 $m^2$/gm and preferably from 200 to 250 $m^2$/gm.

DESCRIPTION OF PREFERRED EMBODIMENTS

The invention is now further described with particular reference to the following non-limiting examples which illustrate the capabilities of the media of the invention for effective removal of contaminants from hydrocarbon streams.

In the Examples that follow analysis was done using ICP with identification of the individual elements carried out by Metro Tech System Ltd. of Calgary, Canada.

Examples 1–4 all use a hydrocarbon stream identified by an API gravity of 48 containing various amounts of metallic contaminants. This stream was pumped through a heated stainless steel column 25 cm in length and 1.27 cm in diameter, packed with 8 gm of the media. In each case the media had the following properties. The BET surface area of the media obtained was measured at 219 $m^2$/gm, the apparent porosity was 78.5%, the water absorption was 103.4%, the apparent specific gravity was 3.54 gm/cc and the material density was 0.76 gm/cc. Analysis of the material showed 92.2% by weight of alumina, 6.6% by weight of calcia and 1.2% by weight of magnesia.

EXAMPLE 1

In a first run of the hydrocarbon stream which contained 24 ppm of iron, 2 ppm of zinc and 2 ppm of lead was passed through the above media at a flow rate of 3.1 mL/min. The initial temperature was held at 273.9° C. and after 60 hours the temperature was raised to 301.7° C. and after 120 hours the temperature was raised again to 315.6° C. The amounts of metals removed, as a percentage of the ppm of the element in the flow, after the specified number of hours is as indicated in the following Table 1.

TABLE 1

| HOURS | LEAD | IRON | ZINC |
| --- | --- | --- | --- |
| 6 | 100 | 87 | 100 |
| 12 | 100 | 85 | 100 |
| 24 | 24 | 81 | 100 |
| 36 | 14 | 88 | 100 |
| 48 | 38 | 95 | 100 |
| 60* | 100 | 98 | 100 |
| 72 | 100 | 98 | 100 |
| 84 | 100 | 100 | 100 |
| 96 | 33 | 96 | 100 |
| 108 | 39 | 97 | 100 |
| 120* | 38 | 100 | 100 |
| 132 | 39 | 100 | 100 |
| 144 | 39 | 100 | 100 |
| 156 | 96 | 99 | 100 |
| 162 | 100 | 96 | 100 |
| 174 | 78 | 91 | 100 |
| 186 | 100 | 100 | 100 |
| 198 | 83 | 93 | 100 |
| 200 | 91 | 99 | 100 |

*indicates temperature raised.

EXAMPLE 2

After 200 hours the column was cleaned using toluene and regenerated with steam as described above. This run was conducted at 315.6° C. and the flow rate was again 3.1 ml/min. The hydrocarbon stream contained the same level of the same impurities as were used in Example 1. The results are presented in Table 2 with the percentage of the ppm of the element present that have been removed indicated in each column.

TABLE 2

| HOURS | LEAD | IRON | ZINC |
| --- | --- | --- | --- |
| 6 | 100 | 100 | 100 |
| 12 | 100 | 100 | 100 |
| 24 | 100 | 100 | 100 |
| 36 | 100 | 100 | 100 |
| 48 | 100 | 100 | 100 |
| 60 | 100 | 100 | 100 |
| 72 | 100 | 100 | 100 |

TABLE 2-continued

| HOURS | LEAD | IRON | ZINC |
|---|---|---|---|
| 84 | 100 | 100 | 100 |
| 96 | 100 | 100 | 100 |
| 108 | 100 | 100 | 100 |
| 120 | 100 | 100 | 100 |
| 132 | 100 | 100 | 100 |
| 144 | 100 | 100 | 100 |
| 156 | 100 | 100 | 100 |
| 162 | 100 | 100 | 100 |

EXAMPLE 3

After the run lasting 162 hours described in Example 2, the hydrocarbon flow was changed to one containing the following metallic impurities: iron—116 ppm; zinc—2 ppm; lead—3ppm; aluminum—223 ppm; magnesium—49 ppm; sodium—38 ppm; calcium—57 ppm and manganese—1 ppm.

The run was continued for 24 hours under the same conditions described in Example 2. Samples removes at 12 and 24 hours indicated that 100% of each of the impurities had been removed at each interval.

EXAMPLE 4

In this Example the influence of temperature is explored ion the removal of various elements. The same experimental arrangement as was used in the prior Examples was used but with a new charge of media and a hydrocarbon flow containing: mercury—6 ppm; copper—2.6 ppm; iron—8.9 ppm; zinc—0.1 ppm; and phosphorus—8.2 ppm. The flow was continued at a rate of 3.1 mL/min. for six hours at temperatures changed as indicated in Table 3 below.

TABLE 3

| HOURS | 1 | 3 | 5 | 6 |
|---|---|---|---|---|
| TEMP (° C.) | 110 | 210 | 280 | 280 |
| Mercury | 50% | 66% | 77% | 85% |
| Copper | 81% | 96% | 100% | 100% |
| Iron | 0% | 30% | 100% | 100% |
| Zinc | 100% | 100% | 100% | 100% |
| Phosphorus | 100% | 100% | 100% | 100% |

EXAMPLE 5

In this Example evaluation was carried out in a pilot plant using a hydrocarbon stream due for reprocessing. The API gravity of the stream was 45–50, the water content was 1–10% and the solids level was 1–3%. The base water and sediment were removed and the flow was then pumped through two heat exchangers and a line heater to raise the temperature to between 248.9° C. and 315.6° C. The hot flow was then passed through a bed containing approximately 1.87 $m^3$, (66 cubic feet), of the same media used in the prior Examples. The volume of flow processed was between 25 and 38 per day. The pressure on the flow was 517 $kN/m^2$ to 620 $kN/m^2$, (75 to 90 psi), at which pressure at least 50–60% is in the vapor form. The vapor stream is separated and not passed through the media bed. The vapor and the liquid bed were recombined after passing the liquid component through the bed and sent on to a fractionating tower. After a total of 2300 barrels had been processed the percentage of the metals removed was as follows:

phosphorus—98%; sodium—72%; iron 95%; aluminum—97%; copper—92%; zinc—99%; calcium—94%; magnesium—98%; silicon—77%; lead—49%; and chromium 89%.

A sample taken after 1900 barrels had been processed contained iron, calcium, sodium, magnesium, aluminum, silicon and phosphorus. After passage through the bed the percentages of these elements removed was as follows: calcium—90%; sodium—73%; magnesium—98%; aluminum—95%; iron—92%; silicon—15%; and phosphorus—96%.

EXAMPLE 6

In this Example the hydrocarbon flow was a Northern Alberta crude containing zinc, nickel, sodium and vanadium. A sample from this source was placed in an autoclave with 10 gm of the same media used in the previous Examples. The autoclave was heated to 300° C. under 689 $kN/m^2$, (100 psi), nitrogen pressure. After 30 minutes the sample was analyzed and it was found that 45% of the nickel, 21% of the sodium, 76% of the sodium and 24% of the vanadium had been removed.

We claim:

1. A method for the removal of metals from a hydrocarbon stream which comprises contacting the hydrocarbon stream with an absorbent media comprising from 50 to 96% by weight of alumina and from 50 to 4% by weight of alkaline earth metal oxides selected from calcia and magnesia present in calcia to magnesia weight ratios of from 90:10 to 50:50, said media having a BET surface area of at least 100 $m^2/gm$.

2. A method according to claim 1 in which the absorbent media have an apparent porosity of from 60 to 80%.

3. A method according to claim 1 in which the media comprise less than 1% of other metallic or metallic oxide impurities.

4. A method according to claim 1 in which the removal is conducted at a temperature of from 20° C. to 450° C.

5. A method according to claim 4 in which the removal is conducted at a temperature of from 250° C. to 350° C.

* * * * *